United States Patent [19]

Pinhas

[11] 4,038,319
[45] July 26, 1977

[54] SUBSTITUTED PHENOXYALKYLAMINES, PROCESS FOR THEIR PREPARATION AND APPLICATIONS THEREOF

[75] Inventor: Henri Pinhas, Paris, France

[73] Assignee: Laboratoires Laroche Navarron, Levallois, France

[21] Appl. No.: 466,838

[22] Filed: May 3, 1974

Related U.S. Application Data

[63] Continuation-in-part of Ser. No. 210,560, Dec. 21, 1971, Pat. No. 3,843,725.

[51] Int. Cl.$^2$ ............................................. C07C 93/06
[52] U.S. Cl. ............................ 260/570.7; 260/501.18; 260/501.19; 260/570 R; 260/570.6; 260/591; 260/612 D; 424/316; 424/330
[58] Field of Search ...................... 260/501.18, 570.7

[56] References Cited

U.S. PATENT DOCUMENTS

| | | | |
|---|---|---|---|
| 1,894,865 | 1/1933 | Hartmann et al. ................ | 260/570.7 |
| 2,683,719 | 7/1954 | Kerwin et al. ................ | 260/570.7 X |
| 3,437,731 | 4/1969 | Schmitt et al. ................ | 260/570.7 X |
| 3,501,769 | 3/1970 | Crowther et al. ............. | 260/501.17 |

OTHER PUBLICATIONS

Pinhas, "Chemical Abstracts," vol. 76, p. 348, Section No. 14107w, (1972).

*Primary Examiner*—Robert V. Hines
*Attorney, Agent, or Firm*—Oldham & Oldham Co.

[57] ABSTRACT

This invention relates to phenoxyalkylamines having the formula

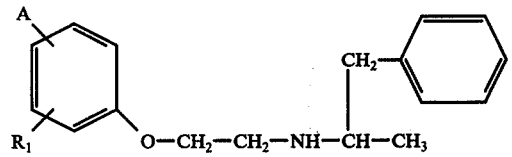

in which $R_1$ is hydrogen, halogens or methyl, A is cyclohexylmethyl, propenyl, butenyl, cyclohexenylmethyl or a group

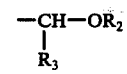

in which $R_2$ is a $C_1$–$C_4$ alkyl radical or methoxy-ethyl, and $R_3$ is ethyl, propyl, cyclohexyl or phenyl and their acid addition salts.

Said phenoxyalkylamines possess coronary vasodilatator and cardiotonic properties.

4 Claims, No Drawings

SUBSTITUTED PHENOXYALKYLAMINES, PROCESS FOR THEIR PREPARATION AND APPLICATIONS THEREOF

This application is a continuation-in-part of the application Ser. No. 210,560 and filed Dec. 21, 1971 and now U.S. Pat. No. 3,843,725.

The present invention relates to phenoxyalkylamines, and to the therapeutic applications thereof.

There is already known a therapeutic composition useful in particular as coronary vasodilatator and as antispasmodic drug, comprising, as active ingredient, a phenoxyalkylamine having the formula:

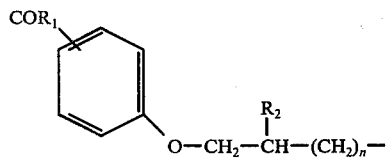

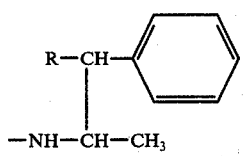

in which $n$ is zero or 1, R is hydrogen or a hydroxy group, $R_1$ is an alkyl group and $R_2$ is hydrogen, a hydroxy group or an alkyl group, $R_2$ being other than hydroxy when $n$ is equal to zero, or a product resulting from hydrogenation of the ketone group $COR_1$ thereof to an alcohol group $CHOHR_1$.

The vasodilatator and spasmolytic properties of said prior phenoxyalkylamines were found to be quite outstanding.

However, there have now been found new phenoxyalkylamines which, while having still better vasodilatator and spasmolytic properties than those — although already exceptional —0 of the prior phenoxyalkylamines, have a better therapeutic ratio than the latter. Phenoxyalkylamines were prepared which exhibit toxicity only at dosage above 500 mg and sometimes up to 1500 mg under the same experimental conditions as those mentioned above.

Said new phenoxyalkylamines according to the invention have the formula:

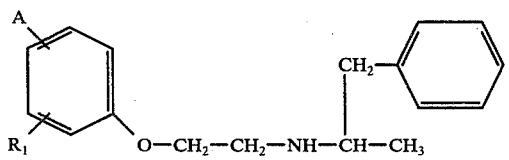

in which $R_1$ is selected from the group consisting of hydrogen, halogens and methyl, A is selected from the group consisting of cyclohexyl methyl, propenyl, butenyl, cyclohexenylmethyl and the

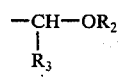

radicals in which $R_2$ is selected from the group consisting of $C_1$-$C_4$ alkyl radicals, and methoxy ethyl and $R_3$ is selected from ethyl, propyl, cyclohexyl and phenyl.

A preferred group of compounds according the present invention consists of the compounds in which A is an unsaturated radical or a

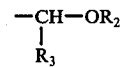

radical. In the case where A is cyclohexenylmethyl, the double bond in the ring may migrate to a juxtanuclear position, thus giving hexylidene methyl.

The phenoxyalkylamines of this invention may also exist in the form of non-toxic acid addition salts thereof with non-toxic inorganic or organic acids and typically as the hydrohalides, particularly the hydrochlorides and hydrobromides, as the nitrates, sulfates, methanesulfonates, lactates, citrates, maleates, tartrates, acetylsalicylates, acetates, oxalates, and the like salts which are readily prepared by reacting compounds (I) as the free base with stoichiometrically equivalent amounts of the selected acid or acids.

Formula (I) always includes at least one asymmetrical carbon atom. It is understood that the invention includes within its scope the optically active and racemic forms of the phenoxyalkylamines having the formula (I).

To prepare said phenoxyalkylamines, α-methylphenethylamine having the formula:

may be condensed with a phenoxy intermediate having the formula:

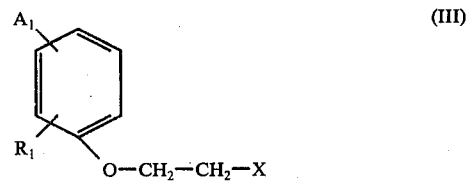

in which A represents a group A or an A-genic group, X is halogen, for example bromine, $R_1$ and A having the above-defined meanings and, when A is an A-genic group, it is converted to a group A.

The term A-genic group denotes any group capable fo giving rise to a group A.

The phenoxyalkylmines of the prior art are exemplary of condensations products carrying an A-genic group.

Their alcohol groups $CHOHR_1$, thus, of $CHOHR_3$ type, may be etherified, for example by heating in alcohol medium ($R_2OH$) in the presence of hydrochloric acid, to give phenoxyalkylamines according to the invention, in which A is

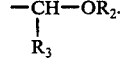

These same alcohol groups, dehydrated in conventional manner with acids (e.g. hydrochloric, sulfuric) or bases (sodium hydroxide), lead to alkenyl compounds according to the invention.

It is understood that it is always possible to prepare first an intermediate compound (III) substituted in the desired manner, and then simply to condense same with α-methyl-phenethylamine, to give the phenoxyalkylamines according to the invention, without any subsequent synthesis step.

This condensation may be carried out under refluxing conditions, within an alcohol solvent, such as ethanol, in the presence of triethylamine or other basic agents which bind the hydrochalic acid formed.

Intermediate compounds (III) are obtained by reacting a phenol compound of the formula:

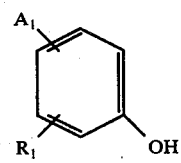

(IV)

with a di-halogenated compound:

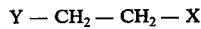

Y being halogen and the other symbols having the aforementioned meanings.

This reaction is preferably conducted under refluxing conditions, within water, in the presence of a stoichiometric amount of metal hydroxide as binding agent for the hydrohalic acid released, for example sodium hydroxide.

The following examples illustrate the invention without, however, limiting same.

EXAMPLE 1

1-[1-ethoxy-propyl]-4-[2-(α-methyl-phenethylamino)-ethoxy]-benzene

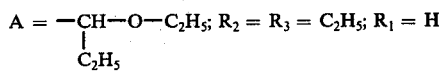

1-(1-hydroxy-propyl)-4-[2-(methyl-α-phenethylamino-ethoxy]-benzene hydrochloride (described in French B.S.M. M-7255) (15 g) is refluxed in an ethanol solution (50 ml) containing 10% of gaseous hydrogen chloride. After refluxing during eight hours, the reaction mixture is concentrated to dryness. It is then recrystallized from ethanol/diethyl ether 1:1, to give 1-(1-ethoxy-propyl)-4-[2-(α-methyl-phenethylamino)-ethoxy]-benzene hydrochloride, in quantitative yield. M.p. = 158°–159° C.

EXAMPLE 2

Substituting methanol for ethanol, 1-(1-methoxy-propyl)-4-[2-(α-methyl-phenethylamino)-ethoxy]-benzene hydrochloride is obtained, under the same conditions, instead of the derivative of Example 1

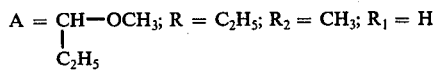

M.p. = 165°–167° C.

EXAMPLE 3

Substituting 1-hydroxy-2-methoxy-ethane for ethanol, 1-[-1-(β-methoxy-ethoxy)-propyl]-4-[2-(α-methyl-phenethylamino)-ethoxy]-benzene hydrochloride is obtained, under the same conditions, instead of the derivative of example 1 M.p. = 190°–192° C.

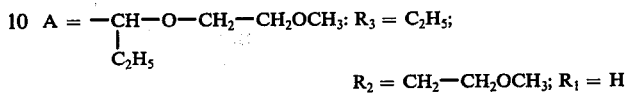

EXAMPLE 4

1-[1-cyclohexyl-1-ethoxy-1)-methyl]-4-[2-(α-methyl-phenethylamino)-ethoxy]-benzene hydrochloride:

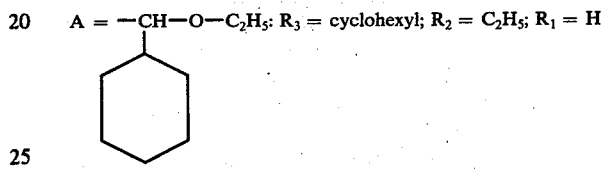

is obtained in ethanol solution containing hydrochloric acid under the conditions described in example 1 from 1-[(1-cyclohexyl-1-hydroxy)-methyl]-4-[2-(α-methyl-phenethylamino)-ethoxy]-benzene described in French Patent Application No. PV 70/46 875 filed by Applicant. It melts at 160°–162° C.

EXAMPLE 5

Substituting 1-hydroxy-2-methoxy-ethane for ethanol, 1-[(1-cyclohexyl-1-β-methoxyethoxy)-methyl]-4-[2-(α-methyl-phenethylamino)-ethoxy]-benzene hydrochloride is obtained under the same conditions described in example 4.

M.p. = 150°–152° C.

($R_3$ = cyclohexyl; $R_2$ = —$CH_2$—$CH_2$—$OCH_3$; $R_1$ = H)

EXAMPLE 6

1'-[α-ethoxy-benzyl]-4'-[2-(α-methyl-phenethylamino)-ethoxy]-benzene:

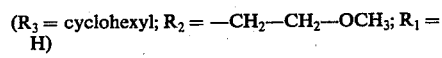

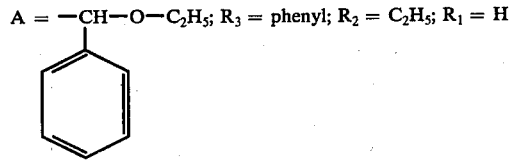

is obtained in ethanol solution containing hydrochloric acid, under the conditions described in example 1, from 1-[α-hydroxy-benzyl]-4-(α-methyl-phenethyliamino)-ethoxy]-benzene described in French Patent Application No. PV 70 46 875 by Applicant. It melts at 156°–158° C.

EXAMPLE 7

1-[α-(β-methoxyethoxy)-benzyl]-4-[2-(α-methyl-phenethylamino)-ethoxy]-benzene hydrochloride melts at 24°–126° C and is obtained by a process similar to that described in example 6.

A = —CH—OCH$_2$—CH$_2$OCH$_3$; R$_3$ = phenyl;

R$_2$ = (CH$_2$)$_2$OCH$_3$; R$_1$ = H

EXAMPLE 8

1-Propenyl-4-[2-(α-methyl-phenethylamine)-ethoxy]-benzene and its hydrochloride

A = —CH = CH—CH$_3$; R$_1$ = H

Procedure 1

4-(2-bromo-ethoxy)-1-propenyl-benzene is first prepared. (III) : A = —CH = CH—CH$_3$; R$_1$ = H;X = Br p-Hydroxy-propenyl-benzene (0.1 mole) is dissolved in water (100 ml) containing sodium hydroxide (0.1 mole). 1,2-Dibromo-ethane (0.13 mole) is then added thereto.

The product, b.p.$_1$ = 120°–122° C is obtained after refluxing during 24 hours and the usual treatment.

The bromo derivative (0.05 mole), α-methylphenethylamine (0.05 mole) and triethylamine (0.15 mole) in ethanol are then refluxed during 48 hours. The alcohol solvent is removed in vacuo. The residue is dissolved in an organic solvent, such as diethyl ether or ethyl acetate. Hydrochloric acid (ca. 10% solution) is then added to the well stirred solution. The resulting crystals are suction filtered. The hydrochloride after recrystallization frm ethanol melts at about 145°–148° C.

Procedure 2

1-[(1-hydroxy-propyl)]-4-[2-(α-methyl-phenethylamino)-ethoxy]-benzene (ca. 0.01 mole) (described in French B.S.M. M-7255) is refluxed during about 10 hours, in the presence of potassium hydrogen sulfate (0.1 mole) in water (ca. 100 ml).

The same hydrochloride, melting at about 145°–148° C, is obtained after conventional treatment.

EXAMPLE 9

1-[(1-cyclohexenyl)-methyl]-4-[2-(α-methylphenethylamino)-ethoxy]-benzene hydrochloride or 1-[cyclohexylidene-methyl]-4-[2-(α-methyl-phenethylamino)-ethoxy]-benzene hydrochloride is prepared, using the procedure 1 described in example 8.

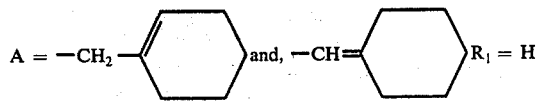

The double bond of the cyclohexenyl may migrate in the side-chain, and an equilibrium is found to become established between both said isomeric forms.

The product melts at 152°–156° C.

EXAMPLE 10

3'-methyl-1'-[(1-cyclohexenyl)-methyl]-4-[2-(α-methyl-phenethylamino)-ethoxy]-benzene hydrochloride, which melts at 160°–163° C, is prepared using the procedure 1 of example 8.

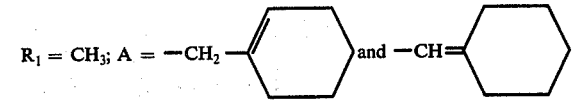

EXAMPLE 11

1-[cyclohexyl-methyl]-4-[2-(α-methyl-phenethylamino)-ethoxy]-benzene hydrochloride.

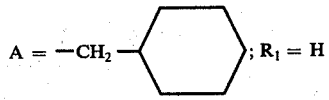

is prepared using the procedure 1 of example 8. It melt at about 184°–187° C.

EXAMPLE 12

3-Chloro-[(1-cyclohexyl-1-ethoxy)-methyl]-4-[2-(α-methyl-phenethylamino)- ethoxy]-benzene hydrochloride is prepared using the procedure 1 of example 8.

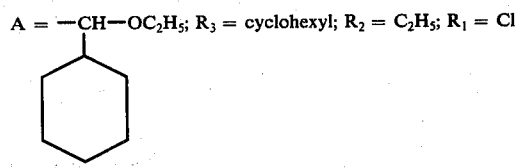

This product melts at about 165°–170° C.

EXAMPLE 13

1[1-ethoxy-butyl]-4-[2-(α-methyl-phenethoylamino)-ethoxy]-benzene is prepared using the procedure 1 of example 8.

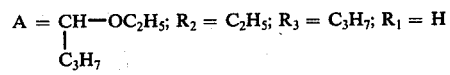

The hydrochloride of this compound melts at 164°–165° C

EXAMPLE 14

Substituting butanol for ethanol in example 1, 1-[1-butoxypropyl]-4-[2-(α-methyl-phenethylamino)-ethoxy]-benzene hydrochloride is obtained under the same conditions.

M.p. = 177°–180° C.

EXAMPLE 15

1-Butenyl-4-[2-(α-methyl-phenethylamino)-ethoxy]-benzene

A = —CH = CH—CH$_2$—CH$_3$; R$_1$ = H

This compound is obtained by a procedure similar to procedures 1 or 2 of example 8.

The hydrochloride melts at 190°–192° C.

Each and every of the compounds enumerated in Example 1 through 15 above, is a desirable or preferred compound according to the present invention.

The results of toxicological and pharmacological tests demonstrating the safe character and the activity of the phenoxyalkylamines of this invention are given below.

I - ACUTE TOXICITY

The acute toxicities of said materials were investigated orally, in Swiss mice and Sprague Dawley rats.

The animals are fasted 18 hours prior to the single administration of the product and are kept under supervision 14 days during which their behavior and death rate were noted.

The $LD_{50}$ of said products, investigated in both species and calculated according to the method according to Litchfield and Wilcoxon are of the order of from 500 to 1500 mg/kg.

II - CORONARY DILATATOR ACTION

1. On the isolated heart - Langendorff's method.

The tests were carried out on the hearts of Fauve de Bourgogne (about 2 kg) rabbits. The hearts are rapidly taken out and maintained in surviving condition by perfusion of a physiological (Tyrode type) liquid heated at 37° C and oxygenated under a constant pressure of 50–60 cm of water. Perfusion of the hearts was effected counter-currently, and volumetric determinations of the coronary rate of flow were recorded at thirty second intervals.

After stabilization of the basic rate of flow, the products, dissolved in physiological saline solution, are injected in a volume of from 0.05 to 0.2 ml.

Dose-action curves were established from the various results obtained.

The products produce a marked increase of the coronary rate of flow which is apparent at a dosage of 10 $\gamma$; a 50% increase of the original rate of flow is obtained, depending on the test products, at a dosage comprised within the range from 15 $\gamma$ to 100 $\gamma$.

2. On the whole animal

The tests were carried out in male and female dogs having a weight between 10 and 15 kg.

After chloralose-induced anesthesia, the animals are placed under artificial respiration.

The carotid pressure is recorded, together with the cardiac frequency and the electrocardiogram.

The coronary flux is investigated by means of a nycotron.

The test materials were dissolved in physiological saline solution and administrated by the intravenous route.

Increase of the coronary flux is observed at dosages from 0.5 to 2 mg/kg.

III - ACTION ON CONTRACTILE STRENGTH

The tests were carried out either in the whole animal, or in the isolated heart.

Dogs, both male and female, are anesthetized with chloralose.

Systemic blood pressure is recorded at the level of the carotid with an electric/sensor.

The contractile strength of the heart was measured with a strain gauge attached to the wall of the right ventricle.

The products, dissolved in physiological saline solution, are administered intravenously (external saphenous vein).

The phenoxyalkylamines of this invention produce an increase of the contractile strength of the heart which becomes more marked with time. Generally, this action has a duration of over one hundred minutes. The cardiotonic action is apparent at dosages from 0.5 to 2 mg/kg.

The products were tested on the isolated heart of rabbit maintained in surviving condition by Langendorff's method. Cardiac stimulation is apparent at dosages of about 200 $\gamma$.

IV - SPASMOLYTIC ACTION

The spasmolytic action was studied in vitro with a fragment of duodenum of rat maintained in surviving condition in an oxygenated physiological liquid. Inhibition of 50% of the contraction due to effusion of a given dose of acetylcholine and barium was studied. The $ED_{50}$ of the test products is comprised within a range from 20 to 65 $\gamma$ with respect to acetylcholine-induced contraction, and within a range from 15 to 80 $\gamma$ with respect to barium-induced contraction.

It is apparent from such tests that the phenoxyalkylamines of this invention and their non-toxic salts are useful in human thereapeutics as coronary vasodilatator, cardiotonic and spasmolytic drug.

Therefore, the present invention provides also a pharmaceutical composition having coronary vasodilatator, cardiotonic and spasmolytic activities containing a therapeutically effective quantity of a compound according to the present invention.

These compounds are useful for the treatment of cardiovascular disorders.

In such applications, the compound is advantageously administered orally, at a dosage of from 150 to 750 mg per 24 hours.

Any formulations suitable for this route of administration may be used, the active ingredient being admixed with a pharmaceutically acceptable carrier or excipient.

An example of such a formulation is given: Tablets containing each:
 50 mg (average dose)
 100 mg (strong dose)
Excipients:
 Talc
 Lactose
 Mg stearate, q.s. to make 1 tablet.

Having now described my invention what I claim and desire to secure by Letters Patent is:

1. A compound selected from the group consisting of phenoxyalkylamines having the formula

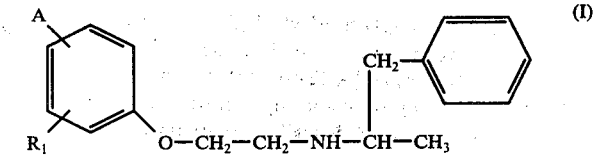

in which $R_1$ is selected from the group consisting of hydrogen and methyl, and A is a cycloalkyl alkyl.

2. A compound according to claim 1 wherein said phenoxyalkylamine is 1-[(1-cyclohexenyl)-methyl]-4-[2-($\alpha$-methylphenethylamino)-ethoxy]-benzene and its non-toxic acid addition salts.

3. A compound according to claim 1 wherein said phenoxyalkylamine is 3'-methyl-1'-[(1-cyclohexenyl)-methyl]-4-[2-($\alpha$-methyl-phenethylamino)-ethoxy]-benzene and its non-toxic acid addition salts.

4. A compound according to claim 1 wherein said phenoxyalkylamine is 1-[cyclohexyl-methyl]-4[2-($\alpha$-methyl-phenethylamino)-ethoxy]-benzene and its non-toxic acid addition salts.

* * * * *